United States Patent
Socha et al.

(10) Patent No.: US 10,417,359 B2
(45) Date of Patent: Sep. 17, 2019

(54) OPTICAL METROLOGY OF LITHOGRAPHIC PROCESSES USING ASYMMETRIC SUB-RESOLUTION FEATURES TO ENHANCE MEASUREMENT

(71) Applicant: ASML NETHERLANDS B.V., Veldhoven (NL)

(72) Inventors: Robert John Socha, Campbell, CA (US); Thomas I. Wallow, San Carlos, CA (US)

(73) Assignee: ASML Netherlands B.V., Veldhoven (NL)

( * ) Notice: Subject to any disclaimer, the term of this patent is extended or adjusted under 35 U.S.C. 154(b) by 423 days.

(21) Appl. No.: 15/379,473

(22) Filed: Dec. 14, 2016

(65) Prior Publication Data

US 2017/0177760 A1  Jun. 22, 2017

Related U.S. Application Data

(60) Provisional application No. 62/268,976, filed on Dec. 17, 2015.

(51) Int. Cl.
*G06F 17/50* (2006.01)
*G06N 20/00* (2019.01)
(Continued)

(52) U.S. Cl.
CPC ..... *G06F 17/5009* (2013.01); *G01N 21/4785* (2013.01); *G03F 7/2002* (2013.01);
(Continued)

(58) Field of Classification Search
CPC .......... G01N 21/4785; G01N 2201/127; G03F 7/2002; G03F 7/2004; G03F 7/70616;
(Continued)

(56) References Cited

U.S. PATENT DOCUMENTS

| 7,042,551 B2 | 5/2006 | Ausschnitt |
| 7,080,330 B1 | 7/2006 | Choo et al. |

(Continued)

FOREIGN PATENT DOCUMENTS

| EP | 1 881 374 | 1/2008 |
| JP | 2008028389 | 2/2008 |

(Continued)

OTHER PUBLICATIONS

International Search Report and Written Opinion dated Mar. 1, 2017 in corresponding International Patent Application No. PCT/EP2016/079063.

(Continued)

*Primary Examiner* — Mark R Gaworecki
(74) *Attorney, Agent, or Firm* — Pillsbury Winthrop Shaw Pittman LLP

(57) ABSTRACT

A process of calibrating a model, the process including: obtaining training data including: scattered radiation information from a plurality of structures, individual portions of the scattered radiation information being associated with respective process conditions being characteristics of a patterning process of the individual structures; and calibrating a model with the training data by determining a ratio relating a change in one of the process characteristics to a corresponding change in scattered radiation information.

26 Claims, 7 Drawing Sheets

(51) Int. Cl.
*G01N 21/47* (2006.01)
*G03F 7/20* (2006.01)
*G06F 17/18* (2006.01)
*G06N 7/00* (2006.01)

(52) U.S. Cl.
CPC ........ *G03F 7/2004* (2013.01); *G03F 7/70616* (2013.01); *G03F 7/70625* (2013.01); *G03F 7/70633* (2013.01); *G06F 17/18* (2013.01); *G06N 7/005* (2013.01); *G06N 20/00* (2019.01); *G01N 2201/127* (2013.01); *G06F 2217/16* (2013.01)

(58) Field of Classification Search
CPC .. G03F 7/70633; G06F 17/18; G06F 17/5009; G06F 2217/16; G06N 7/005
See application file for complete search history.

(56) References Cited

U.S. PATENT DOCUMENTS

| | | | |
|---|---|---|---|
| 7,642,019 B2 | 1/2010 | Kim | |
| 7,791,727 B2 | 9/2010 | Den Boef et al. | |
| 7,916,284 B2 | 3/2011 | Dusa et al. | |
| 8,250,498 B2 | 8/2012 | Huang et al. | |
| 8,806,388 B2 | 8/2014 | Parikh | |
| 8,830,447 B2 | 9/2014 | Den Boef et al. | |
| 8,908,147 B2 | 12/2014 | Den Boef et al. | |
| 9,182,682 B2 | 11/2015 | Cramer et al. | |
| 9,223,911 B2 | 12/2015 | Meiring et al. | |
| 2005/0168716 A1 | 8/2005 | Ausschnitt | |
| 2006/0033921 A1 | 2/2006 | Den Boef et al. | |
| 2006/0234136 A1 | 10/2006 | Kim | |
| 2008/0018874 A1 | 1/2008 | Dusa et al. | |
| 2009/0153818 A1* | 6/2009 | Chauhan | G03B 27/42 355/53 |
| 2009/0157577 A1* | 6/2009 | Chauhan | G03F 7/705 706/16 |
| 2011/0185324 A1 | 7/2011 | Huang et al. | |
| 2011/0231167 A1* | 9/2011 | Cramer | G03B 27/52 703/2 |
| 2011/0249247 A1 | 10/2011 | Cramer et al. | |
| 2012/0013881 A1 | 1/2012 | Den Boef et al. | |
| 2012/0123748 A1* | 5/2012 | Aben | G03F 7/70483 703/2 |
| 2013/0073070 A1 | 3/2013 | Tsai et al. | |
| 2013/0254724 A1 | 9/2013 | Parikh | |
| 2015/0045935 A1 | 2/2015 | Cao et al. | |
| 2015/0213161 A1 | 7/2015 | Meiring et al. | |

FOREIGN PATENT DOCUMENTS

| | | |
|---|---|---|
| JP | 2013012773 | 1/2013 |
| JP | 2013535819 | 9/2013 |
| JP | 2016066091 | 4/2016 |
| JP | 2016523359 | 8/2016 |
| WO | WO 2013/079270 | 6/2013 |
| WO | WO 2013/189724 | 12/2013 |
| WO | WO 2014/082938 | 6/2014 |
| WO | WO 2015/090839 | 6/2015 |

OTHER PUBLICATIONS

Kevin Lensing et al., "Lithography Process Control Using Scatterometry Metrology and Semi-Physical Modeling", Metrology, Inspection, and Process Control for Microlithography XX, Proc. of SPIE, vol. 6518, Apr. 4, 2007, pp. 651804-1-651804-12.

Peng Yu et al., "True Process Variation Aware Optical Proximity Correction with Variational Lithography Modeling and Model Calibration", Journal of Micro-nanolithography Mems and Moems, 36 pages (2007).

Japanese Office Action issued in corresponding Japanese Patent Application No. 2018-5320067, dated Jun. 18, 2019.

* cited by examiner

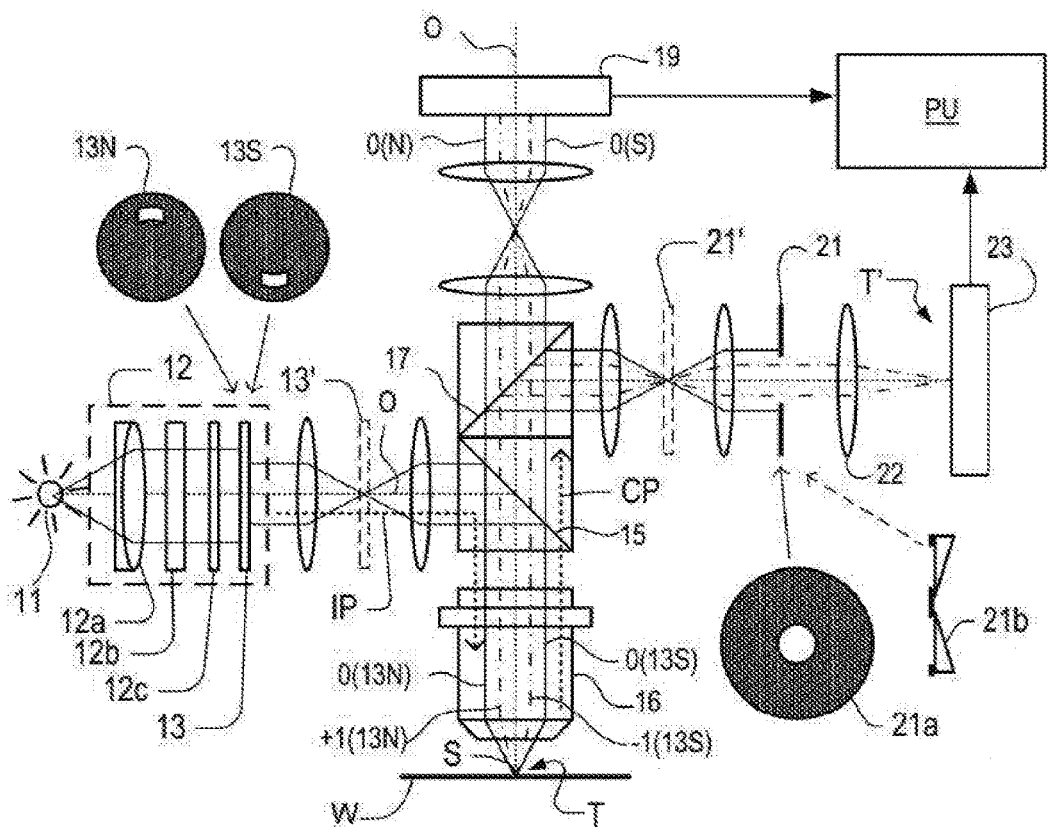
Fig. 5B
Fig. 5A
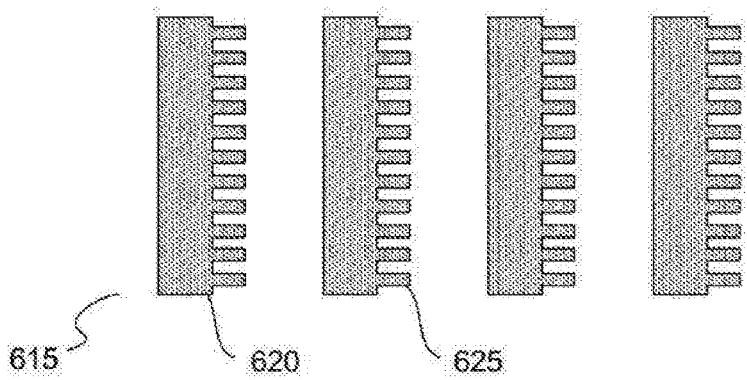
Fig. 6

OPTICAL METROLOGY OF LITHOGRAPHIC PROCESSES USING ASYMMETRIC SUB-RESOLUTION FEATURES TO ENHANCE MEASUREMENT

CROSS REFERENCE TO RELATED APPLICATIONS

This application claims priority and benefit under 35 U.S.C. § 119(e) to U.S. Provisional Patent Application Ser. No. 62/268,976, entitled "Optical Metrology of Lithographic Processes Using Asymmetric Sub-Resolution Features to Enhance Measurement," filed on Dec. 17, 2015, the content of which is incorporated herein in its entirety by reference.

FIELD

The present description relates generally to lithography and, more specifically, to metrology of lithographic processes.

BACKGROUND

A lithographic apparatus, such as a photolithographic apparatus, is a machine that applies a pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a device pattern to be formed on an individual layer of the IC. This pattern can be transferred onto a target portion (e.g., a field including part of, one, or several dies) on a substrate (e.g., a silicon wafer). Transfer of the pattern is typically via imaging onto a layer of radiation-sensitive material (resist) provided on the substrate. In general, a single substrate will contain a set of adjacent target portions that are successively patterned.

In lithographic processes, it is desirable frequently to measure the structures created, e.g., for process control and monitoring. Various tools may make such measurements, including optical tools, like various forms of scatterometers. These devices typically direct a beam of radiation onto a target (e.g., a test structure on a patterned substrate) and measure properties of the scattered radiation. Examples of such properties include intensity of scattered radiation at a single angle of reflection as a function of wavelength; intensity at one or more wavelengths as a function of reflected angle; or polarization as a function of reflected angle. Measured properties often characterize a diffraction "spectrum" from which a property of interest of the target can be determined.

SUMMARY

The following is a non-exhaustive listing of some aspects of the present techniques. These and other aspects are described in the following disclosure.

Some aspects include a process of calibrating a model, the process including: obtaining training data including scattered radiation information from a plurality of structures, individual portions of the scattered radiation information being associated with respective process conditions being characteristics of a patterning process of the individual structures; and calibrating, using one or more processors, a model with the training data by determining a ratio relating a change in one of the process characteristics to a corresponding change in scattered radiation information.

Some aspects include a process of inferring a parameter of a patterning process, the process including: obtaining a scattered radiation measurement of a patterned structure on a substrate; and inferring, using one or more processors and a calibrated model, a process characteristic of the patterning based on the measurement, wherein the calibrated model comprises a ratio relating a change in one of the process characteristics to a change in scattered radiation measurement.

BRIEF DESCRIPTION OF THE DRAWINGS

The above-mentioned aspects and other aspects of the present techniques will be better understood when the present application is read in view of the following figures in which like numbers indicate similar or identical elements:

FIGS. 5A and 5B illustrate schematically an inspection apparatus adapted to perform angle-resolved scatterometry and dark-field imaging inspection methods;

FIG. 6 illustrates target forming elements (e.g., on a reticle) suitable for forming a grating on a substrate having focus dependent asymmetry;

Figure 1:
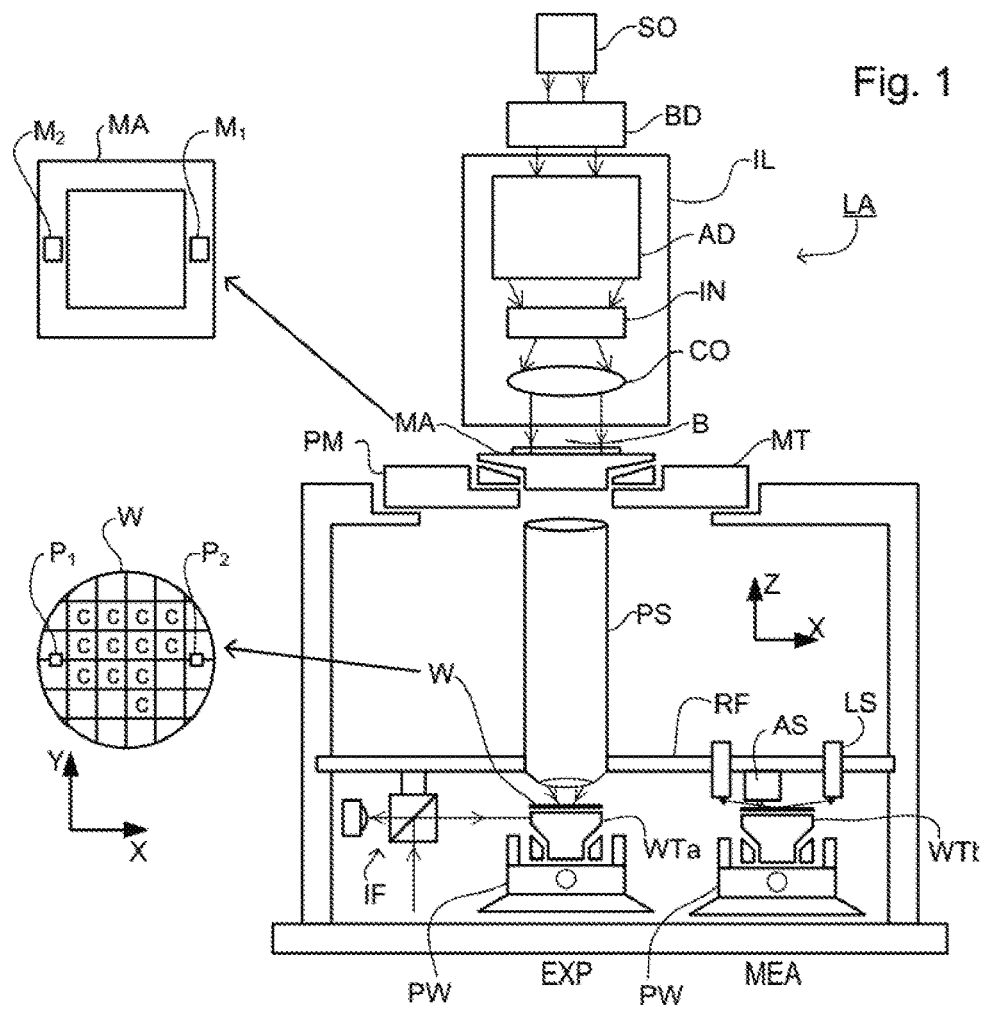
FIG. 1 depicts an example of a lithographic apparatus.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

To mitigate problems described herein, the inventors had to both invent solutions and, in some cases just as importantly, recognize problems overlooked (or not yet foreseen) by others in the field of lithography. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Before describing embodiments in detail, it is instructive to present an example environment in which embodiments may be implemented.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

In some embodiments, the patterning device support holds the patterning device in a manner that depends on the orientation of the patterning device, the design of the lithographic apparatus, and other conditions, such as for example whether or not the patterning device is held in a vacuum environment. The patterning device support can take many forms. The patterning device support may position the patterning device, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example, if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are expected to increase the numerical aperture of projection systems.

In operation, the illuminator IL receives a radiation beam from a radiation source SO. The source and the lithographic apparatus may be separate entities, for example, when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example, when the source is a mercury lamp. The source SO and the illuminator IL, together with the beam delivery system BD if required, are an example of a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., reticle/mask) MA with respect to the path of the radiation beam B, e.g., after mechanical retrieval from a mask library, or during a scan.

Patterning device (e.g., reticle/mask) MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the patterning device alignment marks may be located between the dies. Relatively small alignment mark may also be included within dies, in amongst the device features, in which case it is often desirable that the markers be as small as possible and not require any different imaging or process conditions than adjacent features. The alignment system, which detects the alignment markers, is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, for example, a step mode. In "maskless" lithography, a programmable patterning device is held stationary but with a changing pattern, and the substrate table WT is moved or scanned.

Combinations and/or variations on the above described modes of use or entirely different modes of use may also be employed.

The illustrated example lithographic apparatus LA is of a so-called dual stage type, which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements may be used instead of the dual-stage arrangement shown. For example, other lithographic apparatuses in which a substrate table and a measurement table are provided. These are docked together when performing preparatory measurements, and then undocked while the substrate table undergoes exposure.

Figure 2:
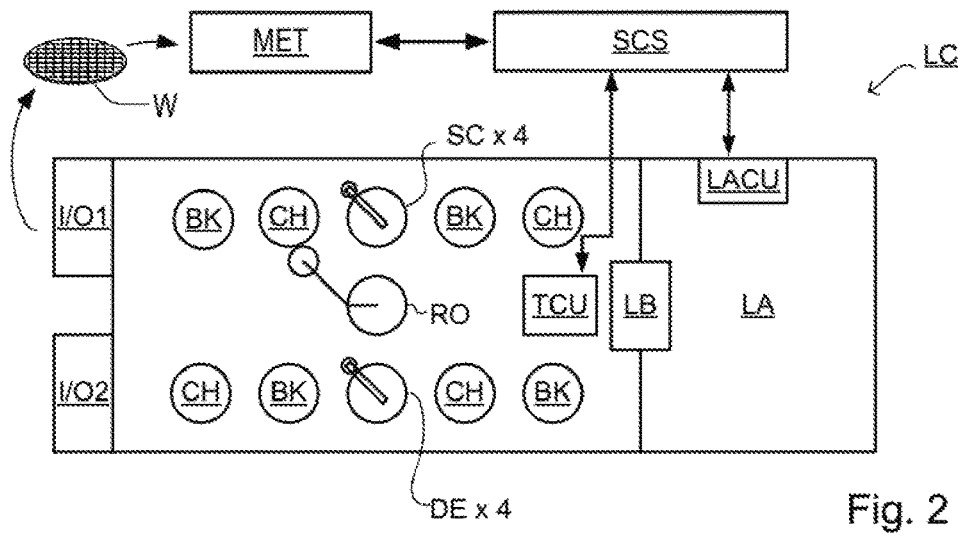
FIG. 2 depicts an example of a lithographic cell, or cluster, in which an inspection technique as described herein may be used.

As shown in FIG. 2, the lithographic apparatus LA forms part of a lithographic cell LC, also sometimes referred to a lithocell or cluster, which also includes apparatus to perform pre- and post-exposure processes on a substrate. Generally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is often desirable to inspect exposed substrates to measure properties such as overlay errors between subsequent layers, line thicknesses, critical dimensions (CD), etc. Accordingly a manufacturing facility in which lithocell LC is located may also include metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To expedite measurements, it is often desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
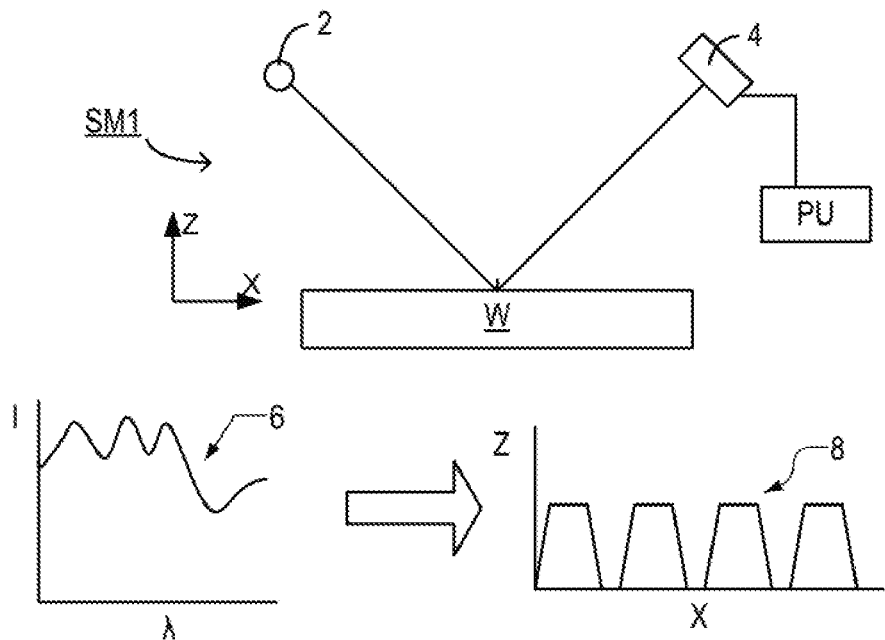
FIG. 3 illustrates principles of operation of a spectroscopic scatterometer as an example of an inspection apparatus.

FIG. 3 depicts an example of a spectroscopic scatterometer, which may be used as an inspection apparatus in a metrology system of the type described above. In some implementations, scatterometer includes a broadband (white light) radiation projector 2, which projects radiation onto a substrate W. The reflected radiation is passed to a spectrometer 4, which measures a spectrum 6 (intensity as a function of wavelength) of the specular reflected radiation. From this data, the structure or profile 8 giving rise to the detected spectrum may be reconstructed by calculation within processing unit PU (which may include one or more of the computer systems described below). The reconstruction can be performed, for example, by Rigorous Coupled Wave Analysis and non-linear regression, or by comparison with a library of pre-measured spectra or pre-computed simulated spectra. In general, for the reconstruction, the general form of the structure is known and some parameters are assumed from knowledge of the process by which the structure was made, leaving fewer parameters of the structure to be determined from the scatterometry data. Such a scatterometer may be configured as a normal-incidence scatterometer or an oblique-incidence scatterometer.

Figure 4:
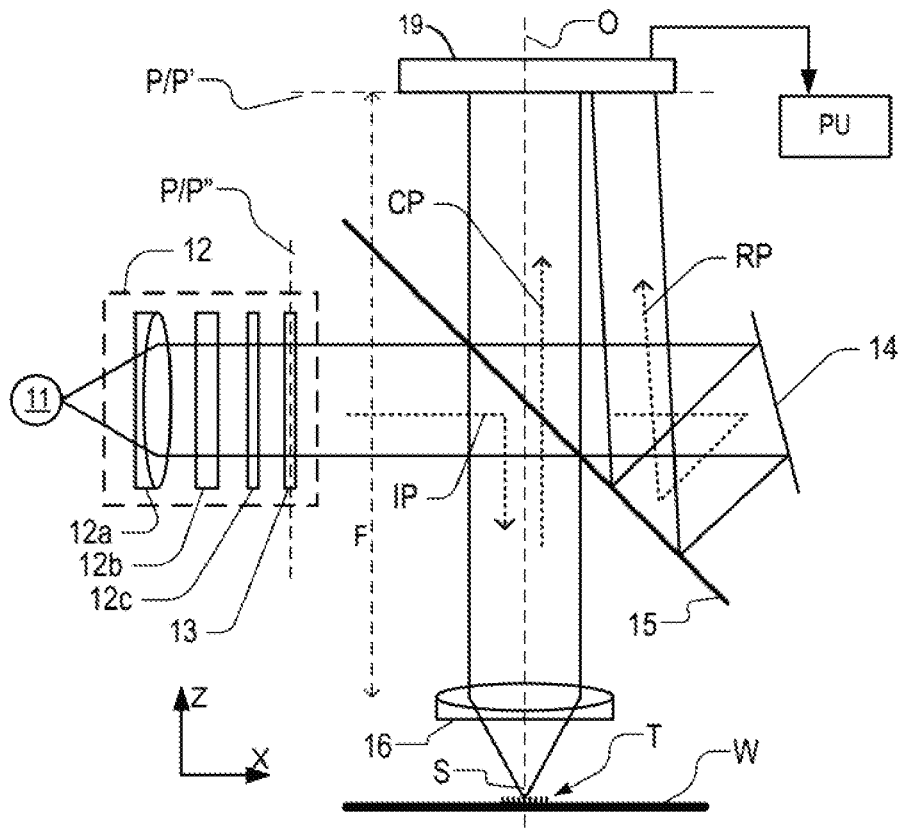
FIG. 4 illustrates in schematic form an angle-resolved scatterometer as another example of an inspection apparatus.

FIG. 4 shows elements of an example of an angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired.

As in the lithographic apparatus LA, one or more substrate tables may be provided to hold the substrate W during measurement operations. The substrate tables may be similar or identical in form to the substrate tables WTa, WTb of FIG. 1. (In an example where the inspection apparatus is integrated with the lithographic apparatus, they may even be the same substrate tables.) Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle whether one or both of those is moving in the real world.

When the radiation beam is incident on the beam splitter 16, in this example, part of it is transmitted through the beam splitter and follows a reference path RP towards a reference mirror 14.

In this example, radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP may be projected onto a different part of the same detector 19 or alternatively on to a different detector (not shown). A reference beam is often used for example to measure the intensity of the incident radiation, to allow normalization of the intensity values measured in the scatter spectrum.

The various components of illumination system 12 can be adjustable to implement different metrology "recipes" within the same apparatus. Color filter 12b may be implemented, for example, by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P'" conjugate with pupil plane P of objective lens 16 and the plane of the detector 19. In this way, an illumination profile defined by the aperture device defines the angular distribution of radiation incident on substrate radiation passing through different locations on aperture device 13.

The detector 19 may measure the intensity of scattered radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

Where a metrology target T is provided on substrate W, this may be a 1-D grating, which is printed such that after development, the bars are formed of solid resist lines. The target may be a test structure designed to be readily measured by the illustrated scatterometer. The target may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the shape of the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of a focus parameter (for example, the focus during exposure of the target) from targets which print with a focus dependent asymmetry. The concepts of asymmetry measurement using the instrument of FIG. 3 or 4 are described for example in U.S. Patent Pub. 20060066855, the contents of which are hereby incorporated by reference. Generally, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 4, where detector 19 may be an image sensor, such asymmetry in the diffraction orders appears directly as asymmetry in the pupil image recorded by detector 19. This asymmetry can be measured by digital image processing in unit PU, and from this, focus can be determined, in some implementations.

FIG. 5A shows in more detail an inspection apparatus implementing angle-resolved scatterometry by the same principles as the apparatus of FIG. 4, with additional adaptations for performing so-called dark field imaging. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating T and diffracted rays are illustrated in more detail in FIG. 5B.

The same reference numbers are used for components described already in the FIG. 4 apparatus. The illumination path is labeled IP as before. The reference path RP is omitted, for clarity. Compared with that apparatus, a second beam splitter 17 divides the collection path into two branches. In a first measurement branch, detector 19 records a scatter spectrum or diffraction spectrum of the target exactly as described above. This detector 19 may be referred to as the pupil image detector.

In the second measurement branch, imaging optical system 22 forms an image of the target on the substrate W on sensor 23 (e.g. a CCD or CMOS sensor). An aperture stop 21 is provided in a plane that is in the collection path in a plane conjugate to the pupil-plane (it may also be called a pupil stop). Aperture stop 21 can take different forms, just as the illumination aperture can take different forms. Typically, aperture stop 21 function to block the zeroth order diffracted beam so that the image of the target formed on sensor 23 is formed only from the first order beam(s). This is the so-called dark field image, similar to dark field microscopy. The images captured by sensors 19 and 23 are output to image processor and controller PU, the function of which will depend on the particular type of measurements being performed.

In the illumination path in this example, additional optics are shown such that a field stop 13' can be placed in a plane conjugate with the plane of the target and the image sensor 23. This plane may be referred to as a field plane, or conjugate image plane, and has the property that each spatial position across the field plane corresponds to a position across the target. This field stop may be used, for example, to shape the illumination spot for a particular purpose, or simply to avoid illuminating features that are within the field of view of the apparatus but not part of the target of interest. The following drawings and discussion refer, by way of example, to techniques for implementation of the function of aperture device 13, but the present disclosure also encompasses use of the same techniques to implement the function of field stop 13'.

As shown in more detail in FIG. 5B, in some examples, target grating T is placed with substrate W normal to the optical axis O of objective lens 16. In the case of an off-axis illumination profile, A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (sufficient to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Different modes of illumination are possible by using different apertures. Apertures 13N ('north') and 13S ('south') each provide off-axis illumination from a specific narrow range of angles only. Returning to FIG. 5A, this is illustrated by designating diametrically opposite portions of the annular aperture as north (N) and south (S). The +1 diffracted rays from the north portion of the cone of illumination, which are labeled +1 (13N), enter the objective lens 16, and so do the −1 diffracted rays from the south portion of the cone (labeled −1 (13S)). As described in the prior applications mentioned in the introduction, using the dark-field imaging senor 23 while switching between apertures 13N, 13S of this type is one way of obtaining asymmetry measurements from multiple small targets. Aperture stop 21a can be used to block the zeroth order radiation when using off-axis illumination.

While off-axis illumination is shown, on-axis illumination of the targets may instead be used and an aperture stop with an off-axis aperture is used to pass substantially only one first order of diffracted radiation to the sensor. In one example, prisms 21b are used in place of aperture stop 21 which have the effect of diverting the +1 and −1 orders to different locations on sensor 23 so that they can be detected and compared without making two images. This technique, is disclosed in the above-mentioned U.S. Patent Application Publication No. 2011-0102753, the contents of which are hereby incorporated by reference. 2nd, 3rd and higher order beams (not shown in FIG. 5A or B) can be used in measurements, instead of or in addition to the first order beams.

When monitoring a lithographic process, it is often desirable to monitor focus of the lithography beam on the substrate. One known method of determining the focus setting from a printed structure is by measuring the critical dimension (CD) of the printed structure. CD is a measure of the smallest feature (e.g., line width of an element). The printed structure may be a target, such as a line-space grating, formed specifically for focus monitoring. It is known that CD usually displays $2^{nd}$ order response to focus, forming what is known as a "Bossung curve" on a plot of CD (y-axis) against focus (x-axis). A Bossung curve is a substantially symmetrical curve which is substantially symmetrical around a peak representing the best focus. The Bossung curve may be substantially parabolic in shape. There are several drawbacks to this approach, which is not to imply that this approach cannot be used with some embodiments. One drawback is that the method shows low sensitivity near best focus (due to the parabolic shape of the curve). Another drawback is that the method is insensitive to the sign of any defocus (as the curve is largely symmetrical around best focus). Also this method is sensitive to inter alia dose and process variation (crosstalk).

To address these issues, diffraction based focus (DBF) was devised. Diffraction based focus may use target forming features provided by a patterning device to print targets having a degree of asymmetry that is dependent on the focus setting during printing. This degree of asymmetry can then be measured using, for example, a scatterometry based inspection method, for example, by measuring the intensity asymmetry between the intensities of $+1^{st}$ and $-1^{st}$ order radiation diffracted from the target, to obtain a measure of the focus setting.

FIG. 6 illustrates a DBF test structure, or target, 615 configured for diffraction based focus measurements. It comprises plural DBF structures 620, each of which comprises high resolution substructures 625. The high resolution substructures 625 on top of a base pitch creates an asymmetric resist profile for each DBF structure 620, with the degree of asymmetry being dependent upon focus. Consequently, a metrology tool can measure the degree of asymmetry from a target formed using DBF target forming design 615 and translate this into the lithographic apparatus focus.

While the DBF test structure 615 enables diffraction based focus measurements, it may not be suitable for use in some situations. EUV resist film thicknesses are significantly lower than those used in immersion lithography, which makes it difficult to extract accurate asymmetry information from the asymmetric profile of the structures forming part of a target. In addition such structures may not comply with the strict design constraints applicable to certain product structures. During the chip making process all features of a patterning device pattern should print and stand up to subsequent processing steps. Semiconductor manufacturers use design rules as a means to restrict the feature designs to ensure the printed features conform to their process requirements. An example of such a design rule relates to the allowable size of structures or pitches. Another example design rule relates to pattern density, which may restrict the density of a resulting resist pattern to be within a particular range. In some cases, these issues may be exacerbated by use of negative tone resist, which are becoming more widely adopted.

Some embodiments may implement a test structure that provides a relatively strong response to variations in focus, exposure, or other characteristics of lithographic processes, while complying with commonly applied design rules. Some embodiments may place sub-resolution features to pattern an isolated line iso-focal (with relatively large depth-of-focus tolerance) or to pattern the isolated line with relatively large exposure latitude. In some cases, this test structure may facilitate use of optical metrology, which is often preferable over other types of measurement, such as destructive measurements, or electron-beam measurements that are either slower, more expensive, less informative in certain ways, or damaging to production substrates (which is not to suggest that those techniques may not also be used in some embodiments). In some cases, the test structure may be implemented by a patterning device, and a measurement model may be calibrated to the test structure by 1) patterning a substrate with the patterning device under varying conditions of a focus exposure matrix; 2) optically measuring the test structures with a metrology tool (such as a scatterometry tool); and 3) fitting the model to the corresponding process conditions and optical measurements. Later, this model may be used to infer unknown process conditions experienced by production substrates through optical measurements of those substrates.

As explained in greater detail, in some embodiments, the test structures include a grating in which the bars of the grating are flanked by asymmetrically distanced sub-resolution assist features extending parallel (e.g., substantially parallel) to the respective bars. These sub-resolution features are expected to cause the sidewalls of the bars when patterned on the substrate to be differently affected depending upon process conditions, such as focus, exposure, or the like. Differences in sidewall shape are expected to provide a relatively robust signal indicative of process conditions to optical metrology tools.

Figure 7:
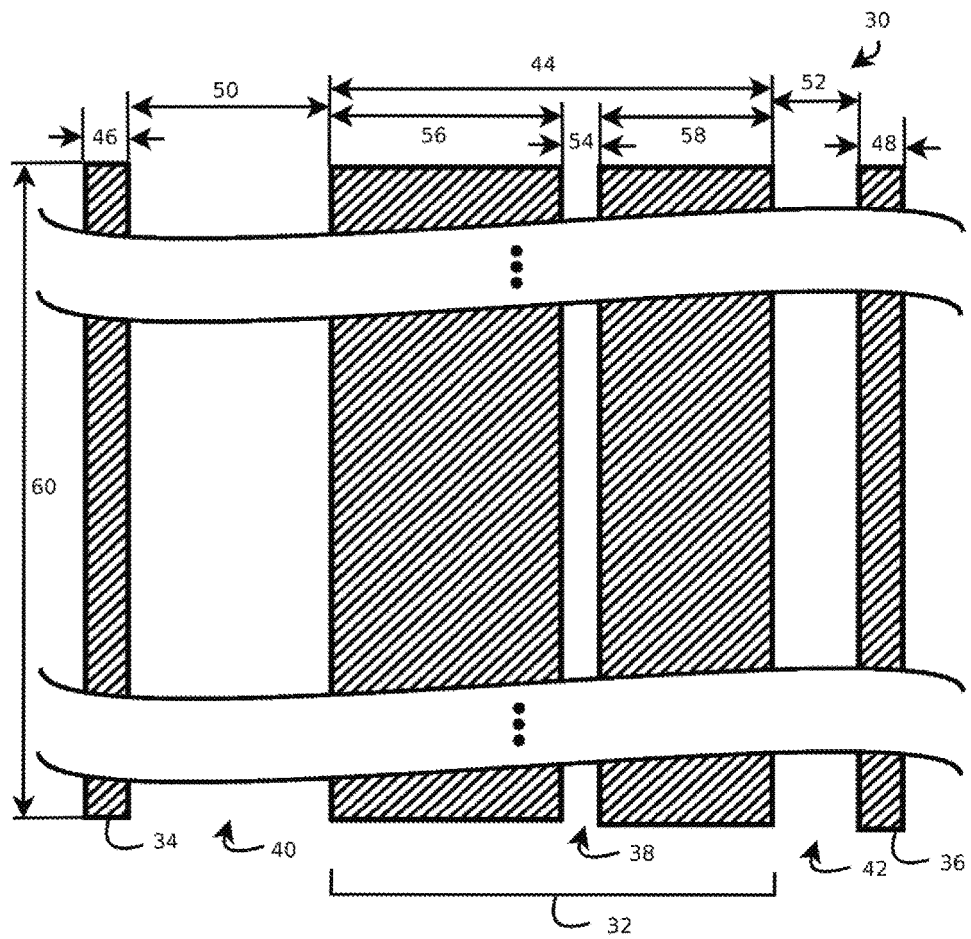
FIG. 7 is a plan view of an example of a patterning device pattern of a test structure in accordance with some embodiments.

FIG. 7 schematically illustrates a portion of an example test structure 30 in accordance with these techniques. In some cases, the test structure 30 resides within a grating of a measurement site on a patterning device pattern. In some embodiments, the test structure 30 includes a main feature 32, a plurality of sub-resolution assist features 34 and 36, and a sub-resolution inverse feature 38. The illustrated portion of the test structure 30 is shown with broken lines, but the structure, in some embodiments, may be relatively uniform along its length. In some cases, the portion of the test structure 30 may be repeated in spaced relation in a parallel array to form a grating, with a spacing between the main features 32 corresponding to a pitch of the grating. The sub-resolution assist features 34 and 36 may be spaced away from the main feature 32 by gaps 40 and 42, respectively.

Dimensions of the test structure 30 may be selected to elicit various responses in patterned test structures on a substrate. In particular, some dimensions may be selected to elicit responses that are amenable to optical measurement and correspond to lithographic process conditions. Dimensions may also be selected based on the wavelength of radiation by which the test structure is patterned on a substrate and based on the wavelength(s) of radiation by which the patterned test structure is measured.

As illustrated in FIG. 7, the main feature 32 may have a width 44, and the sub-resolution assist features 34 and 36 may have widths 46 and 48, respectively. These widths may be smaller than the resolution limit of the lithographic apparatus, making the features "sub-resolution," notwithstanding other dimensions of the features that may be larger than this limit. As a result, the features 34 and 36 may not directly transfer to a substrate in a lithographic patterning process.

The features 34 and 36 may, however, be sized and spaced to affect the patterning of the main feature 32. In some cases, features 34 and 36 may be characterized as "scatter bars" or "sub-resolution assist features." The sub-resolution feature 34 may be spaced away from the main feature 32 by a distance 50, and the sub-resolution feature 36 may be spaced away from the main feature 32 by another distance 52. These distances may be selected to cause the features 34 and 36 to affect the patterning of the main feature 32. To enhance this effect, in some embodiments, the main feature 32 may be an isolated feature relative to other instances of the test structure, e.g., in a grating. In some cases, the distances 50 and 52 may be less than the wavelength of radiation by which the test structure is lithographically patterned, e.g., on the order of 10-150 nanometers in a 193-nanometer wavelength process, or proportionally smaller or larger for other wavelengths. In some embodiments, the pitch of the grating may be greater than this wavelength, e.g., greater than twice this wavelength.

The distances 50 and 52 may be different from one another, making features 34 and 36 asymmetric relative to the main feature 32. As a result, in some embodiments, the sub-resolution features 34 and 36 may affect the transfer of the main feature 32 when lithographically forming a patterned test structure on a substrate, and because distances 50 and 52 are different, the effect may be different on the different sides of the main feature 32, as described in greater detail below with reference to FIG. 8.

The sub-resolution inverse feature 38 may be dimensioned to elicit similar effects. In some cases, the width 54 may be less than the lithographic resolution limit, so the feature 38 does not transfer to a substrate. The feature 38 may be disposed within the main feature 32 at different distances 56 and 58 from the sides of the main feature 32. Consequently, the feature 38 is expected to affect the transfer of the pattern of the different sides of the main feature 32 differently, affecting the right side to a greater degree than the left side in the illustrated orientation.

The wavelength of radiation with which a pattern is lithographically transferred may guide the selection of other dimensions. In some embodiments, the width 44 of the main feature 32 is larger than a resolution limit of the radiation with which the pattern is lithographically transferred from the patterning device to the substrate. Thus, the main feature may yield a corresponding patterned test structure on a substrate.

In some embodiments, the dimensions 52 and 50 and 56 and 58 may be selected based on a desired amount of effect from the corresponding sub-resolution feature 34, 38, or 36 on an adjacent sidewall of the main feature 32. Smaller distances 50, 56, 58, and 52 are expected to correspond to larger effects from the sub-resolution features. In some cases, these effects are a function of both these respective distances and a process characteristic of the lithographic process manifests at the surface of a substrate (in contrast to a process setting, which may be different from the process that actually unfolds as process drift occurs). For instance, in some cases depending on the shape of the test structure, the magnitude of the effect may be a function of the distance and one or more selected from: focus, exposure, chromatic aberration, alignment, or spherical aberration. In some cases, the distance effect is proportional to changes in these process conditions, or in some embodiments, the distance effect is non-proportional to the changes in these process conditions. In non-proportional examples, differences between the sidewalls of the pattern main feature are expected to be indicative of the process condition experienced by the substrate, e.g., the difference may increase as focus changes in one direction and decrease as focus changes in the other direction.

Other radiation sources, such as those used in metrology, may guide the choice of some dimensions. In some embodiments, the pitch, e.g., spacing between instances of the main structure 32 in a grating, may be selected based on the radiation with which optical measurements are performed. Similarly, the width 32 of the main feature may be selected based on the metrology radiation.

In some embodiments, the test structure 30 may be a one-dimensional test structure in which the distance 60 is substantially larger (for example, more than one order of magnitude, larger) than the distance 44, and the shape of the test structure may be relatively uniform over distance 60. Or in other embodiments, the shape may vary or be interrupted. Of note, features 34, 36, and 38 are sub-resolution features notwithstanding distance 60 being greater than the resolution limit of a lithographic apparatus.

The shape of test structure 30 is expected to be acceptable under design rules that are expected to be commonly applied, particularly for negative tone resist processes. In the illustrated example, the sub-resolution features 34, 36, and 38 are parallel to the main feature 32 (e.g., substantially parallel for purposes of comparison with design rules and affecting the main feature). This attribute is expected to reduce process integration issues relative to other test structures, such as those described above with reference to FIG. 6, in which some features are orthogonal to a main feature. That said, some embodiments may also use the features shown in FIG. 6, for instance, with the orthogonal structures on one side of the main feature and the sub-resolution assist feature 34 of FIG. 7 on the other side.

The present techniques are suitable for use with both positive tone resist and negative tone resist. With positive tone resist, the resist is exposed to radiation where the underlying material is to be removed, and with negative tone resist, the resist is exposed to radiation where the underlying material is to be preserved, for instance, following a subsequent etch. The terms "main feature" and "assist feature" apply to both domains. In some cases, these features may correspond to a portion of a patterning device pattern that prevents radiation from being transmitted to the substrate or to a portion of a patterning device that permits radiation to be transmitted to the substrate, depending upon the type of resist in use.

Figure 8:
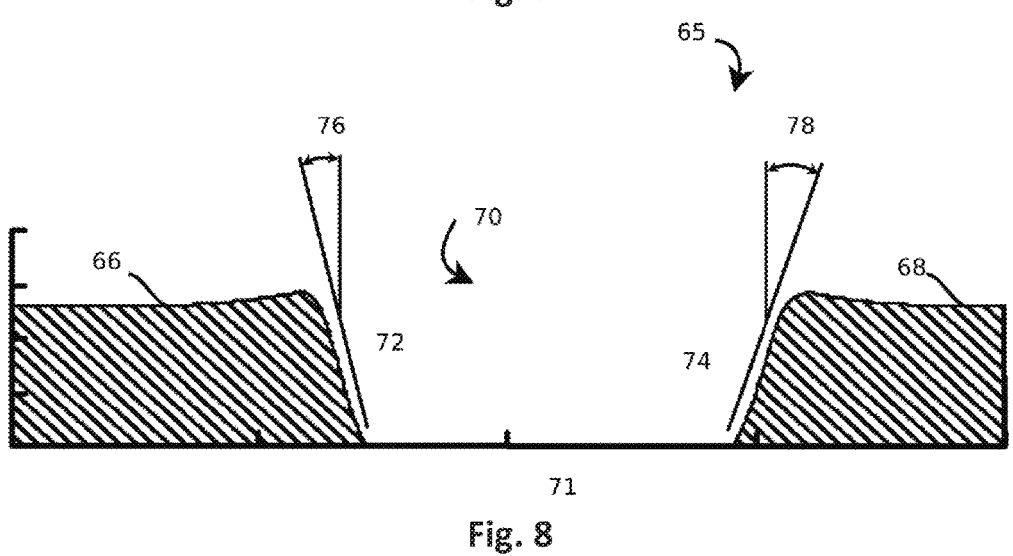
FIG. 8 is a cross-sectional view of an example of a patterned test structure on a substrate corresponding to the pattern of FIG. 7.

FIG. 8 illustrates a simulated resist profile produced by the test structure of FIG. 7 upon a substrate following a lithographic patterning. The illustrated patterned test structure 65 is shown in a cross-sectional view, with dimension 60 being normal to the plane of FIG. 8. The illustrated patterned test structure 65 includes two bodies of resist 66 and 68 on either side of a trench 70 in the resist. These structures may reside upon a substrate underlying in region 71. Trench 70 may correspond to the main feature 32 of FIG. 7. Notably, assist features 34, 38, and 36 are not directly represented in the patterned test structure 65 of FIG. 8, in part, because these features 34, 38, and 36 are smaller than the resolution limit of the lithographic process.

Features 34, 38, and 36, however, affect the shape of the trench 70 in the patterned test structure 65. The trench 70 is defined, in part, by sidewalls 72 and 74. The sidewalls rise at angles 76 and 78, respectively, relative to a normal vector to the substrate 71. As illustrated, the angles 76 and 78 are different, with angle 78 being larger than angle 76 in this example. This difference is believed to be due, in part, to the effects of sub-resolution features 34, 36, and 38 and the relative distances to the respective sidewalls of the main feature 32 in FIG. 7. In some embodiments, the difference between angles 76 and 78 may be affected by the process characteristics of the lithographic process with which the patterned test structure 65 is transferred to the substrate 71.

Often, these process characteristics are specified in settings of a lithographic apparatus, but the actual process characteristics experienced at the surface of the substrate 71 frequently deviate from the settings. For example, attributes like focus and exposure may drift by small, but relevant, amounts over time in ways that are relatively difficult to predict. Any number of factors may cause process characteristics to drift, for example, heating of lenses of the lithographic apparatus, changes in the manufacturing facility environment, changes in an underlying film stack, wearing of consumable components, and the like.

In some embodiments, such drift can be detected optically by measuring the test structure 65, for example, with an ellipsometer, like a scatterometer. The test structure 65 may be repeated in a grid or grating on a measurement location on a substrate, and the above-described measurement techniques may be used to measure attributes of the shape of test structure 65. In some cases, these measurements may include signals indicative of the angles 76 and 78, for instance, measurements indicative of the difference between angle 76 and 78. In some cases, such optical measurements may be relatively fast and inexpensive relative to other techniques by which a test structure may be characterized. For instance, top-down scanning electron microscope measurements often do not provide sufficient information about the shape of sidewall 72 and 74 and can be relatively slow and expensive. Similarly, cross sectioning a substrate is a relatively slow process that can destroy the substrate at issue. This is not, however, to imply that some embodiments may not be used in conjunction with these measurement techniques.

In some cases, the shape of the patterned test structure 65 may depend upon both optical and non-optical effects. For instance, lateral stresses in the resist 66 and 68 produced by shrinkage of the resist may cause the shapes of angle 72 and 74 to shift, as the resist shrinks more than the substrate 71 to which it adheres, and these effects may also be measured, in some embodiments.

In some embodiments, optical measurements of pattern test structure 65 may be correlated to process conditions that tend to produce those shapes, e.g., in a correlative or mechanistic model described below. In some embodiments, after calibration, this model may be used to monitor patterning processes based on observed optical measurements.

It should be noted that the test structure 30 of FIG. 7 and patterned test structure 65 of FIG. 8 are merely exemplary of the present techniques. A variety of other configurations may be used. For example, additional sub-resolution features 34 and 36 may be disposed on either side of the main feature 32 at different distances to enhance the effect of the sub-resolution features. In some embodiments, sub-resolution features 34 or 36 may include an additional sub-resolution feature on its respective side, while the other side does not. In some cases, one sub-resolution feature may be symmetric, while another is asymmetric. In some cases, three or more sub-resolution features may be disposed on one side while being absent from the other. Similar variations may apply to the sub resolution inverse feature 38. For instance, multiple sub-resolution inverse features 38 may be disposed at various positions within the main feature 32. In some cases, these features may be positioned asymmetric relative to the main feature 32 to differently affect the sidewalls of the patterned test structure 65. The illustrated test structure 30 is straight and continuous (e.g., substantially straight and continuous) along dimension 60, but in other embodiments, the patterned test structure 30 may include curves or interrupted portions. In some cases, the main feature may have other shapes, for instance, the main feature may be a pillar or via, and the assist features may extend around the periphery of the pillar or via, in some cases asymmetric to a central axis of the pillar or via. Various other permutations are consistent with these examples.

Figure 9:
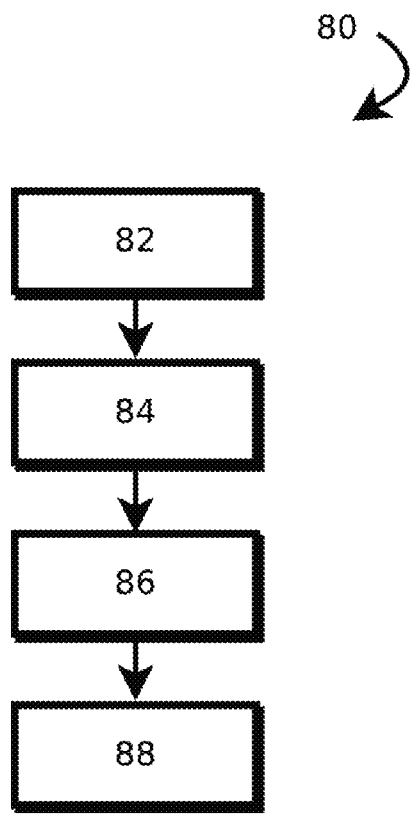
FIG. 9 is a flowchart of an example of a process for calibrating a model based on the test structure of FIG. 7.

FIG. 9 illustrates an example of a process 80 for calibrating a model that infers patterning process characteristics (e.g., as manifest at the surface of a substrate) based on optical measurements, for instance, of the above-described examples of test structures. In some embodiments, the process 80 may include intentionally varying one or more the lithographic process characteristics through a parameter space (for instance, through a matrix of values) and correlating the set points of the process with the observed optical measurements of the test structures patterned under the varying conditions. Such correlation may take a variety of forms, including training a machine learning model, selecting parameters of a model, populating a lookup table, and the like.

In some embodiments, the process 80 includes obtaining a patterning device pattern (e.g., a reticle with such a pattern formed thereon or therein) having a test structure with the main feature and one or more sub-resolution features that are proximate to, asymmetric to, and substantially parallel to, the main feature, as indicated by block 82. In some embodiments, the patterning device pattern may have the test structure of FIG. 7 or one or more of the variations described above. In some embodiments, obtaining a patterning device pattern may include obtaining a lithographic apparatus in which a patterning device has been installed configured to provide the patterning device pattern, for instance, a lithographic apparatus in a semiconductor fabrication plant in which electronic devices are manufactured using the patterning device. In some cases, the test structures may be disposed on a patterning device pattern alongside a layout of a layer for a functioning device, such as an integrated circuit. For instance, the semiconductor manufacturing plant may include a plurality of patterning devices in a plurality of lithographic apparatuses for patterning different layers of the semiconductor devices, and the different patterning device may be used to pattern the different layers.

Next, some embodiments may lithographically pattern a substrate, varying one or more process characteristics of the lithographic process, as indicated by block 84. Patterning a substrate may include patterning one or more substrates, depending upon the desired sample size. Lithographic patterning may include patterning with the above-described lithographic apparatuses to form a patterned test structure, like that of FIG. 8, on the surface of the substrate. Varying the one or more process characteristics may include varying one or more lithographic process characteristics through a range of values. For instance, at fixed or varying increments through the range. In some cases, multiple process characteristics may be varied through multiple respective ranges. For instance, focus and exposure settings may be varied through respective ranges in accordance with a focus-exposure matrix. In some cases, one or more additional process characteristics may be varied in one or more higher dimensional matrices. In some cases, different exposure fields on the substrate may receive different treatments according to the different process characteristic variations. For instance, a first field including, for example, a plurality of dies, may be patterned with a first set of focus and exposure settings, and then a second, different field, for instance, including another instance of the plurality of dies may be patterned with a different focus setting, exposure setting, or both. In some cases, the test structure described above may be disposed within a scribe line between respective dies or disposed within a die. In some embodiments, lithographic patterning may include developing and baking the resist prior to measurement.

Next, some embodiments may optically measure the patterned test structures, as indicated by block 86. Optical measurements may be performed with one or more of the above-described scatterometry techniques. In some cases, a plurality of patterned test structures within each field may be measured to acquire a more robust sample size of the result of each treatment condition. In some embodiments, the optical measurements may include receiving an optical signal indicative of the shape of a first sidewall of the main feature, receiving an optical signal indicative of a shape of a different (second) sidewall of the main feature, and then determining a difference between the optical signals to calculate a differential optical measurement. In some cases, the optical measurements for each treatment condition may be aggregated, for instance, with a measure of central tendency, like a mean, a mode, or a median value, or in some embodiments, the values may be un-aggregated and used to enhance various machine learning techniques, for instance, with cross validation or bootstrap aggregation.

Next, some embodiments may calibrate a model based on the test conditions and corresponding optical measurements, as indicated by block 88. In some cases, a calibration record may include a plurality of the test conditions, each of the test conditions including set-points for the lithographic process using the test condition, and a collection of optical measurements of patterned test structures formed with those test conditions. A variety of different models and calibration techniques may be used. In some cases, the model may be a lookup table with an index corresponding to ranges of optical measurements and values corresponding to the test conditions observed to produce those optical measurements in those ranges. In another example, the model may be built by training a decision tree with the test data. In some cases, calibrating a model based on the test conditions may include updating a pre-existing model, for instance with Bayesian inference to account for the newly observed test data. In some cases, calibrating the model may include calibrating a hidden Markov model with the process characteristics being the hidden state. In some cases, the model may be calibrated a plurality of different times with different subsets of the test data, and the different instances may be compared to one another or aggregated in cross validation to enhance the reliability of the models.

In some embodiments, the model may be based on the following Taylor series expansion:

$$P = P_0 + \frac{\partial P}{\partial \text{focus}} \cdot \text{focus} + \frac{\partial P}{\partial \text{dose}} \cdot \text{dose} + \frac{\partial^2 P}{\partial \text{focus}^2} \cdot \text{focus}^2 \quad (1)$$

wherein P is the observed optical signal in a pupil, e.g., a scatterometry pupil or, e.g., an intensity of radiation, for instance, at a specific range of wavelengths or angle; dose is the dose of radiation at the surface of the substrate; focus is the focus condition at the surface of the substrate; and " . . . " refers to higher order terms extending upon the pattern of terms, and which may be omitted in some cases due to their smaller effect, which is not to imply that other features may not also be omitted.

With equation (1) and the pupil measurements of a metrology tool, some embodiments may select equation parameters (e.g., by selecting partial derivative terms that tend to reduce an error function, for instance, a root-mean-square sum of conditions predicted by the model versus set points in a focus-exposure matrix). In some cases, the model may be trained with a gradient descent, such as a stochastic gradient descent. In some embodiments, the model may be trained for multiple parameters, e.g., some test structures may test for exposure and other test structures may test for focus, and the model may be trained for both process characteristics. In some cases, the optical signal is a differential signal obtained by subtracting the two pupil measurements to calibrate focus deviation to pupil pixel deviation.

A model based on equation (1) may take many forms. In some cases, the model is a portion of equation (1) itself, with coefficients determined based on the training data set, for instance the first three terms of equation (1), the first four terms, five terms, six terms, or more terms. In some cases, the model includes several versions of equation (1), each solved for a different process characteristic. In some cases, the model is a look-up table that approximates equation (1) or a trained machine learning model that approximates equation (1), such as a trained decision tree or neural net, e.g., consistent with the universal approximation theorem.

In some embodiments, the model is constructed with a Markov chain Monte Carlo algorithm, for instance with the Metropolis-Hastings algorithm, as executed by one or more of the computing devices described below. In some embodiments, such algorithms when executed may iteratively construct a Markov chain based on samples that tend to be drawn from relatively high probability regions of the desired probability distribution. Some embodiments may include an initialization step in which a point in parameter space and a probability density are chosen, e.g., randomly for the point and as a Gaussian distribution centered on the chosen point for the probability density. Some embodiments may then iteratively 1) determine a candidate subsequent point in the parameter space based on the probability density by selecting the subsequent point by sampling the probability density; 2) determine an acceptance ratio indicating whether the candidate subsequent point is more probable than the current point; and 3) either accept the candidate subsequent point in response to determining the point to be more probable, or reject the candidate subsequent point in response to determining the point to be less probable. Accepted points may form a Markov chain in the parameter space that randomly walks to relatively high probability regions of the space and tends to remain in those regions. In some embodiments, a threshold amount of the initial states in the chain may be discarded in a "burn-in" period during which the chain migrates to higher probability regions. The resulting Markov chain of points (e.g., higher dimensional vectors) may be used to calculate expected values of various process characteristics of a patterning process with Monte Carlo analysis.

Calibration may include determining coefficients of equation (1) that, for measurements in a training set, make the value P agree with the focus, dose, and/or other process characteristic settings intentionally varied when patterning test structures for a training data set. Agreement, in some cases, may be characterized by an error function or a suitability function, depending on sign, that aggregates error over a set of the training data set's test conditions, e.g., a sum of root-mean-square values, or the like. Some embodiments may iteratively select parameters that tend to reduce to increase agreement between the model and the training set, e.g., according to the partial derivative of each parameter with respect to the measure of agreement, until a change between consecutive iterations is less than a threshold value. Some embodiments may repeat this process from different initial selections of parameters and select the results of the repetition resulting in the closest agreement between the training set and the model to guard against selection of local minima. In some embodiments, the results may be cross validated against training data held in reserve.

In some embodiments, determining the coefficients of equation (1) includes determining a ratio relating a change in one of the process characteristics to a change in pupil-intensity. This may include determining a ratio that relates a change in one, and only one, process characteristic to pupil-intensity. In some embodiments, determining the ratio may also include determining a mixed derivative that relates a change in a subset of the process characteristics to a change in pupil intensity. Some embodiments may also determine a total derivative with respect to pupil intensity. Determining a derivative may include approximating a derivative by relating an incremental change a process characteristic to a measured change in pupil intensity while holding other process characteristics approximately constant, e.g., without changing target values in a lithographic apparatus. Determining a derivative may also include determining the inverse of a derivative.

Figure 10:
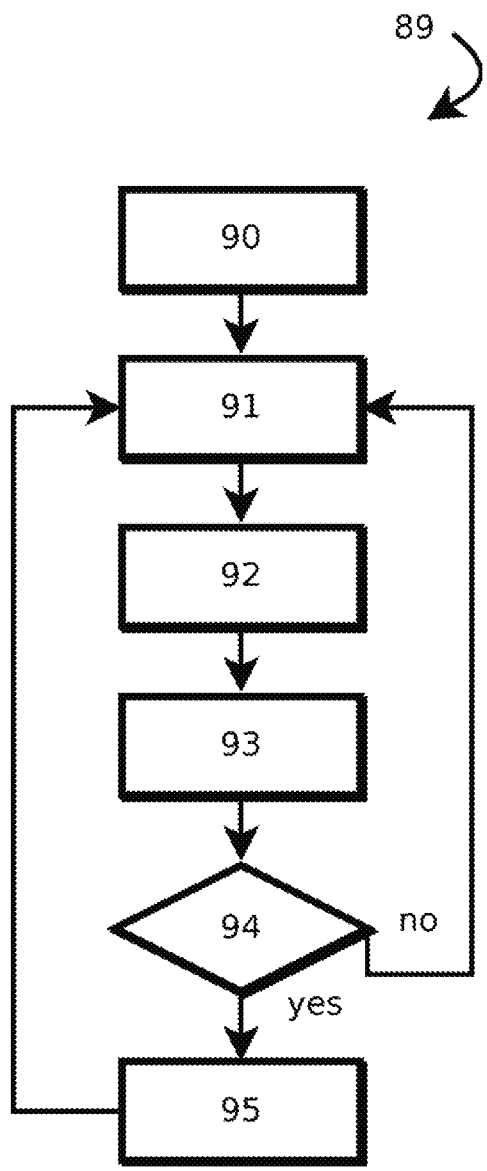
FIG. 10 is a flowchart of an example of a process for monitoring or controlling a patterning process based on the model of FIG. 9.

In some embodiments, once the model is calibrated, the model may be uploaded to a process monitoring module of a lithographic apparatus. This module may include code executing on one or more of the below-described computer systems and that performs the process described below with reference to FIG. 10 to exercise process control or monitor a patterning process.

In some embodiments, the process 89 includes obtaining a patterning device pattern (e.g., a reticle having the pattern therein or thereon) having a test structure with the main feature and one or more sub-resolution features that are proximate to, asymmetric to, and substantially parallel to, the main feature, as indicated by block 90. In some cases, this may be the same patterning device pattern described above. The processes of FIGS. 9 and 10, however, are not limited to the test structures described above with reference to FIGS. 7 and 8 (which is not to imply that other features are so limited). Indeed, these processes are also suitable for use with the test structure of FIG. 6, among others.

Next, some embodiments may lithographically pattern a production substrate (e.g., a substrate having work-in-progress of a manufacturing facility, as opposed to a test substrate) with the patterning device pattern, as indicated by block 91. In some embodiments, this step may include or be part of patterning a plurality of production substrates, for instance, in a collection of production substrates.

Next, some embodiments may optically measure the patterned test structure on the production substrate, as indicated by block 92. In some cases, a subset of production substrates may be selected for measurement representative of the overall production run, or in some cases, each of the substrates in the production run may be measured. In some cases, the optical measurement may be similar or identical to that described above with reference to FIG. 9. In some embodiments, the optical measurement is a scatterometry measurement, and in some cases, the scatterometry measurement produces a differential value indicative of the difference in sidewall shapes of the patterned test structure. In some embodiments, a plurality of locations within a substrate may be measured, for instance, a plurality of locations within each exposure field or within each die.

Next, some embodiments may infer (e.g., estimate through indirect measurement) a process characteristic of the patterning process based on the optical measurements and a model, as indicated by block 93. In some embodiments, this inference may include inputting the optical measurement to the model calibrated with the process of FIG. 9 and outputting the inferred process characteristic. In some cases, the inferred process characteristic is an absolute value, for instance, focus, exposure, chromatic aberration, overlay, and the like. Or in some cases, the inferred process characteristic is a differential, such as a change in one or more of these values. Inferring a process characteristic may include inferring a ratio of process characteristics or some other combination of process characteristics. In some cases, inferring a process characteristic may include inferring a plurality of process characteristics with one model or a plurality of models. In some cases, a plurality of process characteristics may be inferred for each of a plurality of different locations on a substrate, for instance, for each field of the substrate, each die of the substrate, or for each region of each die of a substrate.

Next, some embodiments may determine whether the inferred process characteristic is different from a targeted value, as indicated by block 94. In some cases, the step may include determining whether the inferred process characteristic falls within a threshold of a range of acceptable values, or in some cases, the step may include determining simply whether the values are different at some resolution. In some cases, the step may include determining whether more than a threshold amount (e.g., a count or ratio) of measurement sites have process characteristics that are different from a targeted value, e.g., for a substrate, field, or die. In some cases, a different threshold may be applied to different regions of a substrate, field, or die, e.g., to avoid re-work triggered by measurements of an edge die that is not expected to yield frequently. In some cases, the comparison of a process characteristic to a target value may compare a plurality of process characteristics to a plurality of targeted values, for instance, by calculating a score based on the process characteristics corresponding to acceptable targeted values and cross products of targeted values.

Next, some embodiments may adjust a set point of the patterning process to reduce the difference from the targeted value, as indicated by block 95. In some cases, the step may include adjusting a focus or exposure of the lithographic apparatus to reduce the difference. In some embodiments, this adjustment may reduce drift in process conditions that might otherwise remain undetected for a longer duration of time while additional substrates are processed with less than acceptable process conditions. In some embodiments, the step may additionally or alternatively include reworking a substrate, for instance, by stripping the resist and re-patterning.

In some embodiments, this process 89 may be repeated a plurality of times at various layers in a semiconductor fabrication plant as electronic devices are manufactured. For instance, the substrate may undergo a plurality of cycles of deposition/implant, pattern transfer, etching, and the like to construct the various layers of a semiconductor device, which then may be diced from the substrate, packaged and placed in an electronic device.

The present techniques can be better understood with reference to the following enumerated clauses:

1. A method of calibrating a model, the method comprising: obtaining training data comprising: scattered radiation information from a plurality of structures, individual portions of the scattered radiation information being associated with respective process conditions being characteristics of a patterning process of the individual structures; and calibrating, using one or more processors, a model with the training data by determining a first ratio relating a change in one of the process characteristics to a corresponding change in scattered radiation information.
2. The method of clause 1, wherein calibrating comprises: determining a second ratio relating a change in another one of the process characteristics to a change in scattered radiation information.
3. The method of clause 2, wherein the first ratio is a partial derivative of focus with respect to scattered radiation information or a reciprocal, and wherein the second ratio is a partial derivative of dose with respect to scattered radiation information or a reciprocal.
4. The method of any of clauses 1-3, wherein the model is based on at least three terms of a Taylor series expansion.
5. The method of any of clauses 1-4, wherein the model includes a second order derivative of one of the process characteristics with respect to scattered radiation information or an inverse of the second order derivative.
6. The method of any of clauses 1-5, wherein calibrating the model comprises: determining model parameters with a Markov chain Monte Carlo algorithm.
7. The method of any of clauses 1-6, wherein calibrating the model comprises: determining model parameters with a Metropolis-Hastings algorithm.
8. The method of any of clauses 1-7, wherein calibrating the model comprises: determining model parameters by iteratively adjusting the model parameters based on an aggregate measure of agreement between the respective iteration of the model and at least some of the training data.
9. The method of any of clauses 1-8, wherein the scattered radiation information comprises: a plurality of test conditions indicative of process characteristics of a photolithographic process used to pattern the plurality of test structures on the one or more substrates according to a focus-exposure matrix, with different patterned test structures being patterned under different test conditions, scatterometry pupil-intensity measurements of the plurality of patterned test structures, and data indicating which measurements correspond to which test conditions, and wherein the model infers a characteristic of a photolithographic process from optical measurement of a test structure patterned with the photolithographic process.

10. The method of any of clauses 1-9, wherein the training data comprises simulated training data obtained based on a model of the photolithographic process and a model of the scattered radiation information.

11. The method of any of clauses 1-10, comprising: obtaining a reticle defining, at least in part, the test structure with a main feature and one or more sub-resolution features that are proximate to, and substantially parallel to, the main feature on the reticle; photolithographically patterning the one or more substrates with the reticle.

12. The method of clause 11, wherein the one or more sub-resolution features include a first sub-resolution feature spaced away from the main feature on a first side of the main feature by a first distance sized to affect the corresponding patterned test structure.

13. The method of clause 12, wherein the one or more sub-resolution features include a second sub-resolution feature spaced away from the main feature on a second side of the main feature, different from the first side, by a second distance that is different from the first distance and is sized to affect the corresponding patterned test structure differently from the first sub-resolution feature.

14. The method of any of clauses 11-13, wherein the one or more sub-resolution features include a plurality of sub-resolution features spaced away from the main feature on the same side of the main feature by a plurality of different respective distances each sized to affect the corresponding patterned test structure.

15. The method of any of clauses 11-14, wherein the one or more sub-resolution features include a sub-resolution inverse feature disposed within the main feature a first distance away from a side of the main feature and a second distance away from an opposing side of the main feature, the second distance being different from the first distance.

16. The method of any of clauses 11-15, wherein: the main feature includes a generally straight bar-shaped structure; the one or more sub-resolution features comprise a pair of smaller bar-shaped structures extending along the main feature on opposing sides of the main feature at different distances from the main feature, wherein a width of the smaller bars is smaller than a resolution limit of the photolithographic patterning process, and wherein a width of the main feature is greater than or equal to the resolution limit; the reticle comprises a test grating including a plurality of instances of the test structure in spaced relation to one another; the patterned test structures have sidewalls of different slopes on opposing sides of the bar-shaped structure, and an amount of difference between the slopes varies according to variations of the focus or exposure.

17. The method of any of clauses 11-16, comprising: photolithographically patterning a production run of substrates with the reticle to produce patterned test structures on the production run of substrates along with at a pattern of at least part of production devices; optically measuring at least some of the patterned test structures within the production run before completing the patterning of the production run; inferring process characteristics of the photolithographic patterning of the production run based on the corresponding optical measurements and the correlated model; and determining that a targeted process characteristic is different from an inferred process characteristic.

18. A method of inferring a parameter of a patterning process, the method comprising: obtaining a scattered radiation measurement of a patterned structure on a substrate; and inferring, using one or more processors, a process characteristic of the photolithographic patterning based on the optical measurement with a calibrated model, wherein the model comprises a first ratio relating a change in one of the process characteristics to a change in scattered radiation measurement.

19. The method of clause 18, wherein the first ratio is a partial derivative of focus with respect to scattered radiation measurement or a reciprocal, and wherein model comprises a second ratio that is a partial derivative of dose with respect to scattered radiation measurement or a reciprocal.

20. The method of any of clauses 18-19, comprising calibrating the model by performing steps comprising: obtaining training data comprising: a plurality of test conditions indicative of process characteristics of a photolithographic process used to pattern a plurality of test structures on one or more substrates, with different patterned test structures being patterned under different test conditions, scatterometry pupil-intensity measurements of the plurality of patterned test structures, and data indicating which measurements correspond to which test conditions; and calibrating, using one or more processors, the model with the training data by determining the first ratio.

21. The method of any of clauses 18-20, wherein the structure is a test structure, the method comprising: obtaining a reticle defining the test structure, at least in part, with a main feature and one or more sub-resolution features that are proximate to, and substantially parallel to, the main feature on the reticle; and photolithographically patterning the substrate with the reticle to produce the patterned test structure on the substrate.

22. The method of clause 21, wherein the one or more sub-resolution features include a first sub-resolution feature spaced away from the main feature on a first side of the main feature by a first distance sized to affect the corresponding patterned test structure, and wherein the one or more sub-resolution features include a second sub-resolution feature spaced away from the main feature on a second side of the main feature, different from the first side, by a second distance that is different from the first distance and is sized to affect the corresponding patterned test structure differently from the first sub-resolution feature.

23. The method of clause 21, wherein the one or more sub-resolution features include a sub-resolution inverse feature disposed within the main feature a first distance away from a side of the main feature and a second distance away from an opposing side of the main feature, the second distance being different from the first distance.

24. The method of any of clauses 18-23, comprising: determining that the inferred process characteristic is different from a targeted value; and in response to the determination, adjusting a set-point of the photolithographic patterning process to reduce the difference.

25. The method of any of clauses 18-24, comprising: producing a plurality of electronic or optical devices on the substrate.
26. A system, comprising: one or more processors; and memory storing instructions that when executed by at least some of the processors effectuate operations comprising: obtaining training data comprising: scattered radiation information from a plurality of structures, individual portions of the scattered radiation information being associated with respective process conditions being characteristics of a patterning process of the individual structures; and calibrating, using one or more processors, a model with the training data by determining a first ratio relating a change in one of the process characteristics to a corresponding change in scattered radiation information.
27. A tangible, machine-readable, non-transitory media storing instructions that when executed by one or more processors effectuate the operations of any of clauses 1-25.
28. A system, comprising: one or more processors; and memory storing instructions that when executed by at least some of the processors effectuate the operations of any of clauses 1-25.

Figure 11:
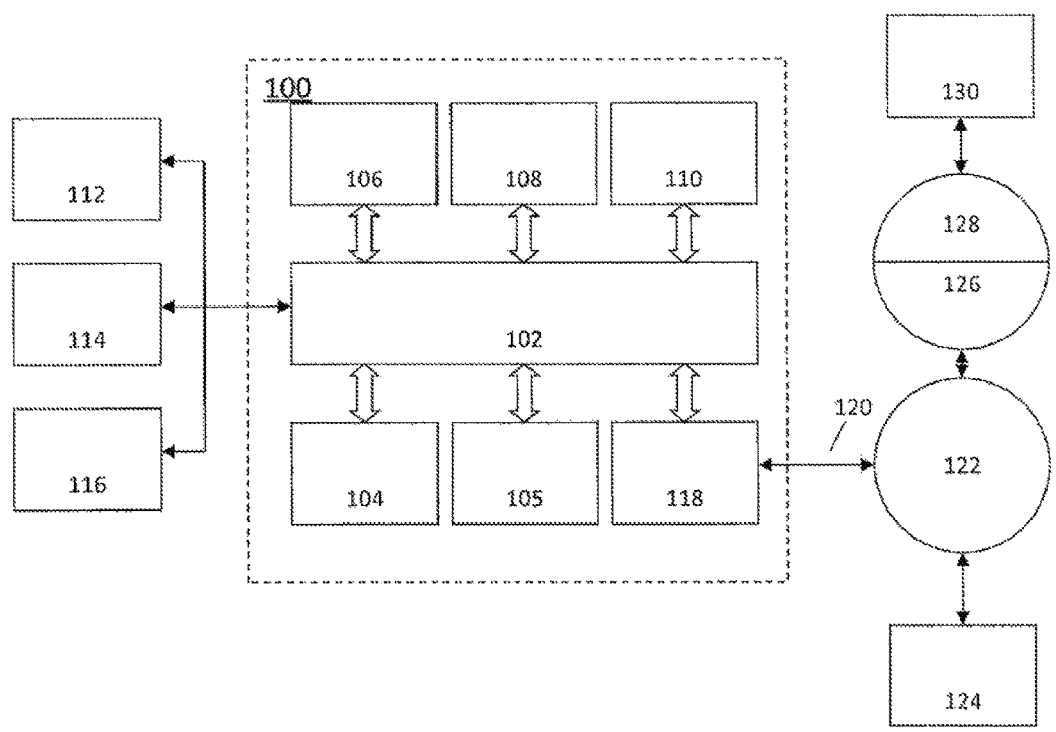
FIG. 11 is a block diagram of an example of a computer system by which certain steps of the above techniques may be implemented.

FIG. 11 is a block diagram that illustrates a computer system 100 which can assist in implementing the methods and flows disclosed herein. Computer system 100 includes a bus 102 or other communication mechanism for communicating information, and a processor 104 (or multiple processors 104 and 105) coupled with bus 102 for processing information. Computer system 100 also includes a main memory 106, such as a random access memory (RAM) or other dynamic storage device, coupled to bus 102 for storing information and instructions to be executed by processor 104. Main memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or flat panel or touch panel display for displaying information to a computer user. An input device 114, including alphanumeric and other keys, is coupled to bus 102 for communicating information and command selections to processor 104. Another type of user input device is cursor control 116, such as a mouse, a trackball, or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane. A touch panel (screen) display may also be used as an input device.

According to one embodiment, portions of a process described herein may be performed by computer system 100 in response to processor 104 executing one or more sequences of one or more instructions contained in main memory 106. Such instructions may be read into main memory 106 from another computer-readable medium, such as storage device 110. Execution of the sequences of instructions contained in main memory 106 causes processor 104 to perform the process steps described herein. One or more processors in a multi-processing arrangement may also be employed to execute the sequences of instructions contained in main memory 106. In an alternative embodiment, hard-wired circuitry may be used in place of or in combination with software instructions. Thus, the description herein is not limited to any specific combination of hardware circuitry and software.

Various forms of computer readable media may be involved in carrying one or more sequences of one or more instructions to processor 104 for execution. For example, the instructions may initially be borne on a computer readable medium of a remote computer. The remote computer can load the instructions into its dynamic memory and send the instructions over a communications line or wirelessly. Computer system 100 can receive the instructions and place the instructions on bus 102. Bus 102 carries the instructions to main memory 106, from which processor 104 retrieves and executes the instructions. The instructions received by main memory 106 may optionally be stored on storage device 110 either before or after execution by processor 104.

In an embodiment, computer system 100 includes a communication interface 118 coupled to bus 102. Communication interface 118 provides a two-way data communication coupling to a network link 120 that is connected to a local network 122. For example, communication interface 118 may be an integrated services digital network (ISDN) card or a modem to provide a data communication connection to a corresponding communications line. As another example, communication interface 118 may be a local area network (LAN) card to provide a data communication connection to a compatible LAN. Wireless links may also be implemented. In any such implementation, communication interface 118 sends and receives electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the worldwide packet data communication network, now commonly referred to as the "Internet" 128. Local network 122 and Internet 128 both use electrical, electromagnetic or optical signals that carry digital data streams. The signals through the various networks and the signals on network link 120 and through communication interface 118, which carry the digital data to and from computer system 100, are example forms of carrier waves transporting the information.

Computer system 100 can send messages and receive data, including program code, through the network(s), network link 120, and communication interface 118. In the Internet example, a server 130 might transmit a requested code for an application program through Internet 128, ISP 126, local network 122 and communication interface 118. One such downloaded application may provide for execution of an embodiment of a portion of process as described herein, for example. The received code may be executed by processor 104 as it is received, and/or stored in storage device 110, or other non-volatile storage for later execution. In this manner, computer system 100 may obtain application code in the form of a carrier wave.

Embodiments of the disclosure may be implemented in hardware, firmware, software, or any combination thereof. Embodiments of the disclosure may also be implemented as instructions stored on a machine-readable medium or computer-readable medium, which may be read and executed by one or more processors. The term "machine-readable medium" or "computer-readable medium" as used herein refers to any medium that participates in providing instructions to processor 104 for execution and/or includes any mechanism configured to store or transmit information in a form readable by a machine (e.g., a computing device). Such a medium may take many forms, including but not limited to, non-volatile non-transitory media, volatile non-transitory media, and transmission media. Non-volatile media include, for example, optical or magnetic disks, such as storage device 110. Volatile media include dynamic memory, such as main memory 106. Transmission media include coaxial cables, copper wire and fiber optics, including the wires that comprise bus 102. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, magnetic disk storage media, or any other magnetic medium, a CD-ROM, DVD or any other optical storage medium, punch cards, paper tape or any other physical medium with patterns of holes, read only memory (ROM), random access memory (RAM), a PROM, an EPROM, a FLASH-EPROM, a flash memory device or any other memory chip or cartridge, a carrier wave (e.g., electrical, optical, acoustical or other forms of propagated signals (e.g. carrier waves, infrared signals, digital signals, etc.) or any other medium from which a computer can read.

Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Although specific reference may be made in this text to the use of the patterning process and/or lithography apparatus in the manufacture of ICs, it should be understood that the patterning process and/or lithography apparatus described herein may have other applications, such as the manufacture of integrated optical systems, guidance and detection patterns for magnetic domain memories, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist) or a metrology or inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of 365, 248, 193, 157 or 126 nm) and extreme ultra-violet (EUV) radiation (e.g. having a wavelength in the range of 5-20 nm), as well as particle beams, such as ion beams or electron beams.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an" element or "a" element includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A method of calibrating a model, the method comprising:
    obtaining training data comprising scattered radiation information from a plurality of structures, individual portions of the scattered radiation information being associated with respective process conditions being characteristics of a patterning process of the individual structures; and
    calibrating, by a hardware processor system, a model with the training data by determining a ratio relating a change in one of the process characteristics to a corresponding change in scattered radiation information.

2. The method of claim 1, wherein calibrating comprises determining a further ratio relating a change in another one of the process characteristics to a change in scattered radiation information.

3. The method of claim 2, wherein the ratio is a partial derivative of focus with respect to scattered radiation information or a reciprocal, and wherein the further ratio is a partial derivative of dose with respect to scattered radiation information or a reciprocal.

4. The method of claim 1, wherein the model is based on at least three terms of a Taylor series expansion.

5. The method of claim 1, wherein the model includes a second order derivative of one of the process characteristics with respect to scattered radiation information or an inverse of the second order derivative.

6. The method of claim 1, wherein calibrating the model comprises determining model parameters with a Markov chain Monte Carlo algorithm.

7. The method of claim 1, wherein calibrating the model comprises determining model parameters with a Metropolis-Hastings algorithm.

8. The method of claim 1, wherein calibrating the model comprises determining model parameters by iteratively adjusting the model parameters based on an aggregate measure of agreement between the respective iteration of the model and at least some of the training data.

9. The method of claim 1, wherein the scattered radiation information comprises:
    a plurality of test conditions indicative of process characteristics of a patterning process used to pattern the plurality of test structures on the one or more substrates according to a focus-exposure matrix, with different patterned test structures being patterned under different test conditions,
    pupil-intensity measurements of the plurality of patterned test structures, and
    data indicating which measurements correspond to which test conditions,
    wherein the model infers a characteristic of a patterning process from optical measurement of a test structure patterned with the patterning process.

10. The method of claim 1, wherein the training data comprises simulated training data obtained based on a model of the patterning process and a model of the scattered radiation information.

11. The method of claim 1, comprising using a patterning device configured to define, at least in part, a test structure having a main feature and one or more sub-resolution features that are proximate to, and substantially parallel to, the main feature, to pattern a substrate with the test structure.

12. The method of claim 11, wherein the one or more sub-resolution features include a first sub-resolution feature spaced away from the main feature on a first side of the main feature by a first distance sized to affect the corresponding patterned test structure.

13. The method of claim 12, wherein the one or more sub-resolution features include a second sub-resolution feature spaced away from the main feature on a second side of the main feature, different from the first side, by a second distance that is different from the first distance and is sized to affect the corresponding patterned test structure differently from the first sub-resolution feature.

14. The method of claim 11, wherein the one or more sub-resolution features include a plurality of sub-resolution features spaced away from the main feature on the same side of the main feature by a plurality of different respective distances each sized to affect the corresponding patterned test structure.

15. The method of claim 11, wherein the one or more sub-resolution features include a sub-resolution inverse feature disposed within the main feature a first distance away from a side of the main feature and a second distance away from an opposing side of the main feature, the second distance being different from the first distance.

16. The method of claim 11, wherein:
the main feature includes a generally straight bar-shaped structure;
the one or more sub-resolution features comprise a pair of smaller bar-shaped structures extending along the main feature on opposing sides of the main feature at different distances from the main feature, wherein a width of the smaller bars is smaller than a resolution limit of the patterning process, and wherein a width of the main feature is greater than or equal to the resolution limit; and
the patterned test structure has sidewalls of different slopes on opposing sides of the generally straight bar-shaped structure, and an amount of difference between the slopes varies according to variations of the focus or exposure.

17. The method of claim 11, comprising:
patterning a production run of substrates to produce patterned test structures on the production run of substrates along with at a pattern of at least part of a production device;
optically measuring at least some of the patterned test structures within the production run before completing the patterning of the production run;
inferring a process characteristic of the patterning process of the production run based on the corresponding optical measurements and a correlated model; and
determining that a targeted process characteristic is different from the inferred process characteristic.

18. A method of inferring a parameter of a patterning process, the method comprising:
obtaining a scattered radiation measurement of a patterned structure on a substrate; and
inferring, by a hardware processor system and using a calibrated model, a process characteristic of the patterning of the patterned structure based on the measurement, wherein the calibrated model comprises a ratio relating a change in a process characteristic to a change in scattered radiation measurement.

19. The method of claim 18, wherein the ratio is a partial derivative of focus with respect to scattered radiation measurement or a reciprocal, and wherein the model comprises a further ratio that is a partial derivative of dose with respect to scattered radiation measurement or a reciprocal.

20. The method of claim 18, comprising calibrating the model, the calibrating comprising:
obtaining training data comprising:
a plurality of test conditions indicative of process characteristics of a patterning process used to pattern a plurality of test structures on one or more substrates, with different patterned test structures being patterned under different test conditions,
pupil-intensity measurements of the plurality of patterned test structures, and
data indicating which measurements correspond to which test conditions; and
calibrating the model with the training data by determining the ratio.

21. The method of claim 18, wherein the structure is a test structure and the method comprises using a patterning device configured to define, at least in part, a test structure having a main feature and one or more sub-resolution features that are proximate to, and substantially parallel to, the main feature, to pattern a substrate with the test structure.

22. The method of claim 21, wherein the one or more sub-resolution features include:
a first sub-resolution feature spaced away from the main feature on a first side of the main feature by a first distance sized to affect the corresponding patterned test structure, and
a second sub-resolution feature spaced away from the main feature on a second side of the main feature, different from the first side, by a second distance that is different from the first distance and is sized to affect the corresponding patterned test structure differently from the first sub-resolution feature.

23. The method of claim 21, wherein the one or more sub-resolution features include a sub-resolution inverse feature disposed within the main feature a first distance away from a side of the main feature and a second distance away from an opposing side of the main feature, the second distance being different from the first distance.

24. The method of claim 18, comprising:
determining that the inferred process characteristic is different from a targeted value; and
in response to the determination, adjusting a set-point of the patterning process to reduce the difference.

25. The method of claim 18, comprising producing a plurality of electronic or optical devices on the substrate.

26. A system, comprising:
a hardware processor system; and
memory storing instructions that when executed by the hardware processor system effectuates operations comprising:
obtaining training data comprising scattered radiation information from a plurality of structures, individual portions of the scattered radiation information being associated with respective process conditions being characteristics of a patterning process of the individual structures; and
calibrating a model with the training data by determining a ratio relating a change in one of the process characteristics to a corresponding change in scattered radiation information.

* * * * *